United States Patent [19]

Geary

[11] Patent Number: 4,465,372
[45] Date of Patent: Aug. 14, 1984

[54] TURBULENCE MEASUREMENT INTERFEROMETER APPARATUS

[75] Inventor: Joseph M. Geary, Edgewood, N. Mex.

[73] Assignee: The Unied States of America as represented by the Secretary of the Air Force, Washington, D.C.

[21] Appl. No.: 422,429

[22] Filed: Sep. 23, 1982

[51] Int. Cl.$^3$ .............................................. G01B 9/02
[52] U.S. Cl. .................................... 356/359; 356/361
[58] Field of Search ............... 356/347, 348, 359, 360, 356/361, 362

[56] References Cited

U.S. PATENT DOCUMENTS 3,567,324  3/1971  Brooks ................................ 356/361
4,180,328 12/1979  Drain ................................. 356/349
4,210,400  7/1980  Misek ................................. 356/359

OTHER PUBLICATIONS

Trolinger et al., "Diagnostics of Turbulence by Holography," *Optical Engineering*, vol. 18, No. 2, pp. 161–166, 4/79.

*Primary Examiner*—James W. Davie
*Assistant Examiner*—Matthew W. Koren
*Attorney, Agent, or Firm*—Donald J. Singer; John R. Flanagan

[57] ABSTRACT

Turbulence measurement interferometer apparatus includes a station having an entrance pupil and an aerodynamically stable boom connected to the station. The station houses an optical mirror arrangement defining an optical axis which extends through the entrance pupil. The boom has an end point spaced from the station but disposed on the optical axis. A laser generates a low power beam which is split into first and second portions. The first portion is guided to the boom end point and launched therefrom as a spherical wavefront through turbulence in front of the entrance pupil and toward the mirror arrangement, which in turn transforms it into an object collimated wavefront. The second portion of the beam is transformed into a second collimated reference wavefront which is combined with the first collimated wavefront and produces an interference pattern which is recorded on a medium, such as a photographic plate. The interference pattern provides information on the turbulence structure present at the entrance pupil of the station.

9 Claims, 4 Drawing Figures

TURBULENCE MEASUREMENT INTERFEROMETER APPARATUS

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention broadly relates to the effects of air turbulence around a high energy laser turret on a high energy laser beam and, more particularly, is concerned with apparatus which applies interferometric techniques to obtain information useful in predicting the degradation of such a beam when it passes through turret induced turbulence.

2. Description of the Prior Art

All types of systems which transmit a coherent optical beam through the earth's atmosphere suffers from distortion caused by the passage of the beam through the atmosphere. More particularly, turbulence in the atmosphere distorts the wavefronts of the optical energy in the beam so that they do not arrive at a remote location as parallel straight lines. This results in the power illuminating a given remote target being reduced.

Similarly, a high energy optical beam generated by a laser on a moving aircraft is affected by the turbulence created by the aircraft. Consequently, it would be desirable to devise some means for gathering data which will be useful in predicting high energy laser performance from airborne platforms in the presence of the turbulence generated as the aircraft moves through the atmosphere. Patents to Brooks, U.S. Pat. No. 3,567,324; and Misek, U.S. Pat. No. 4,210,400 indicate that systems incorporating interferometric techniques have been devised to measure the effects of turbulence on laser-generated energy beams. However, these systems appear to involve laser beam transmissions between stations separated by long distances or between a flying aircraft and a fixed ground station. While these prior art systems may satisfactorily perform their intended functions in the specific applications for which they were designed, a need exists for a measurement apparatus which provides information specifically on the turbulence generated by a high energy laser turret as it moves through the atmosphere.

SUMMARY OF THE INVENTION

The present invention provides a turbulence measurement interferometer apparatus which is designed to satisfy the aforementioned needs. The measurement apparatus generates "in situ" interferometric data on turbulence in the entrance pupil of a turret-like station of the apparatus. The station has the ability to assume many different "look" angles relative to the turbulence, and the apparatus has multiple wavelength capability.

Accordingly, the present invention is directed to a turbulence measurement interferometer apparatus which includes: (a) a station having an entrance pupil and optical means defining an optical axis extending through the pupil; (b) an aerodynamically stable boom connected to the station and having an end point spaced from the station but disposed on the optical axis; (c) a laser for generating a low power beam; (d) means for splitting the beam into first and second portions; (e) means for guiding the first beam portion along a first path to the boom end point from which a first spherical wavefront is launched toward the entrance pupil of the station through air turbulence between the boom end point and the station; (f) the optical means for receiving a portion of the first spherical wavefront and transforming the same into a first collimated wavefront; (g) means for guiding the second beam portion along a second reference path from which is launched a second reference spherical wavefront; (h) means for receiving a portion of the second spherical wavefront and transforming the same into a second collimated reference wavefront; (i) means for combining the first and second collimated wavefronts to form an interference pattern; and (j) means for recording the pattern. The interference pattern provides information on the turbulence structure present at the entrance pupil of the station.

DETAILED DESCRIPTION OF THE INVENTION

Figure 1:
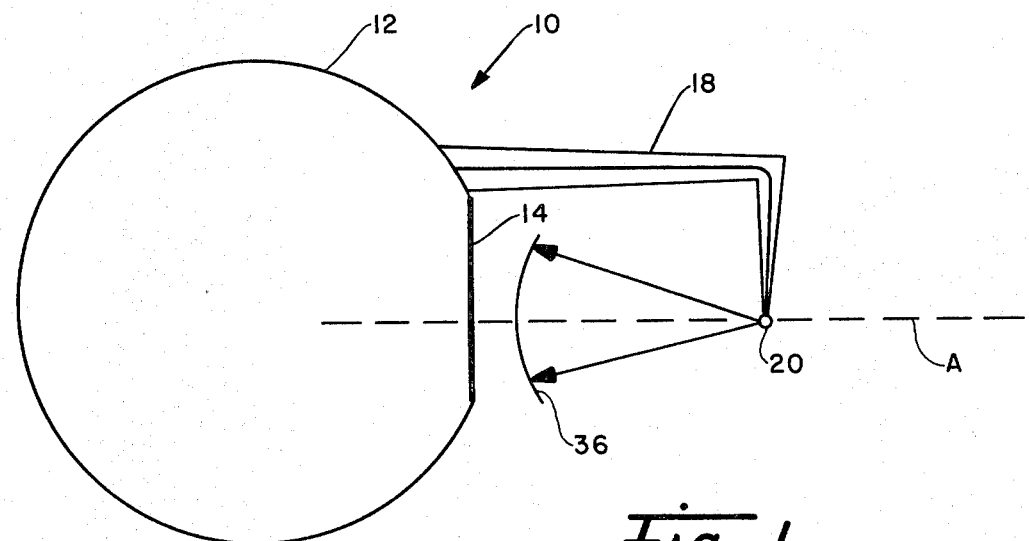
FIG. 1 is a schematic top plan view of the turbulence measurement interferometer apparatus of the present invention.
Figure 2:
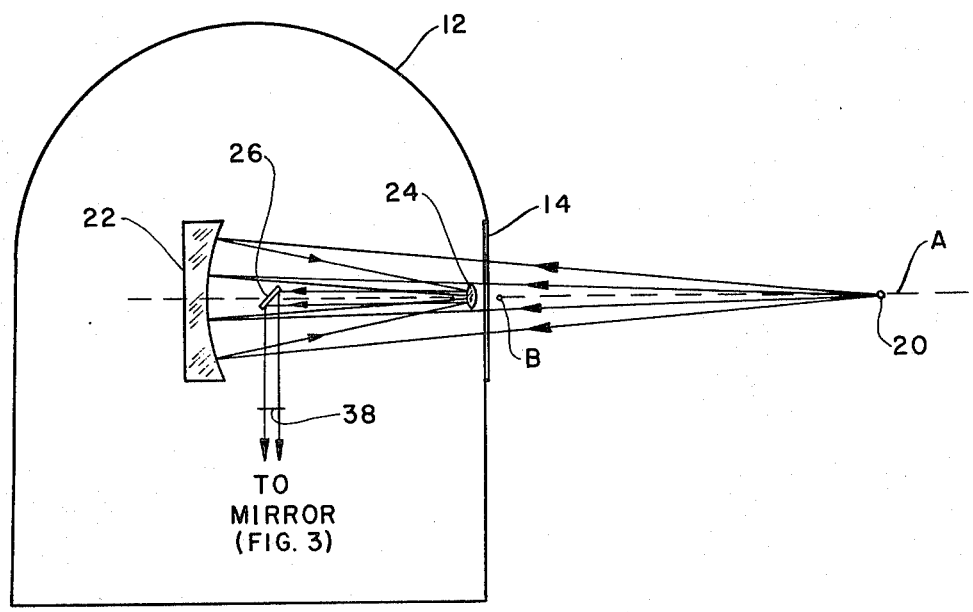
FIG. 2 is a schematic side elevational view of the station of the apparatus of FIG. 1, showing the arrangement of the optical mirrors residing therein.

Referring now to the drawings, and more particularly to FIGS. 1 and 2, there is shown the turbulence measurement interferometer apparatus of the present invention, being generally designated 10. The measurement apparatus 10 includes a turret-like station 12 which is rotatable about orthogonal axes in a conventional manner. The station 12 includes an entrance pupil 14 at one side location thereon which may take the form of an open port or a material window, such as fabricated from zinc selenide, mounted in the port. Also, the station 12 houses optical means 16 (FIG. 2), preferably of the reflective type, which defines an optical axis A extending through the entrance pupil 14.

Attached directly to the station 12 and extending outwardly therefrom is an L-shaped boom 18 of the apparatus 10. The boom 18, designed to be aerodynamically stable, is attached to the station 12 adjacent to the entrance pupil 14 and has an end point 20 spaced from the station but disposed on the optical axis A.

As seen in FIG. 2, a preferred form of the optical means 16 housed within the station 12 includes a large primary mirror 22, a small secondary mirror 24 and a small flat mirror 26. The large mirror 22 is of concave elliptic shape and defines the optical axis A. The mirror 22 is disposed generally at the center of the station 12 remote from, but facing toward, the entrance pupil 14 thereof. The small mirror 24 is of convex parabolic shape, disposed adjacent to the entrance pupil 14, and located on the optical axis A between the large mirror 22 and the entrance pupil 14. The large concave mirror 22 and small convex mirror 24 have a common focus B located on the optical axis A between the end point 20 of the boom 18 and entrance pupil 14. The small flat mirror 26 is disposed on the optical axis A at an acute angle thereto and located between the large mirror 22 and small mirror 24.

Figure 3:
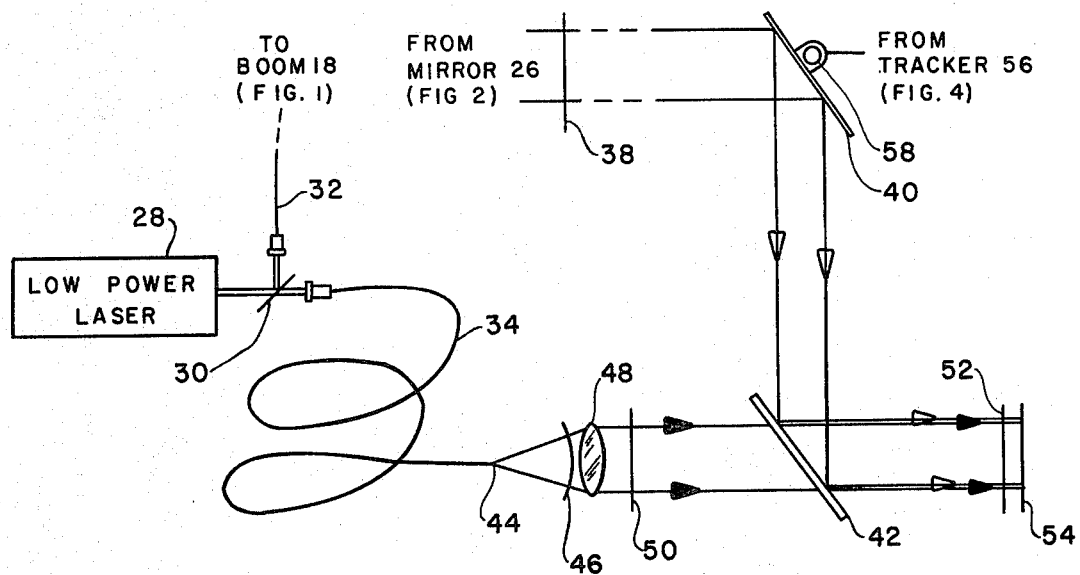
FIG. 3 is a schematic view of the remaining parts of the apparatus which are also contained within the station of the apparatus.

Turning now to FIG. 3, the measurement apparatus 10 also includes within the station 12 a laser 28 for generating a low power beam, a beam splitter 30 for dividing the beam into first and second portions, and first and second guide means 32, 34 of substantially equal length for receiving and transmitting the corresponding first and second beam portions. The guide means 32, 34 may each take the form of a self-focusing optical waveguide, such as a solid fiber optic, wherein a definite phase relationship is maintained in a beam traveling through the waveguide.

The first waveguide 32, running along a first path, extends from the station 12 along the boom 18 (FIG. 1) to its end point 20. At end point 20 a first spherical wavefront 36 is launched toward the entrance pupil 14 of the station 12 through air turbulence located between the boom end point 20 and the station 12. A portion of the first spherical wavefront 36 is received by the large primary concave mirror 22 and reflected toward the small secondary convex mirror 24. These mirrors 22, 24, together forming an arrangement comparable to that of Cassegrain telescope, transform the received portion of the first spherical wavefront 36 into a first, substantially collimated wavefront 38 which as the afocal output of the small flat mirror 26 is diverted from the optical axis A and toward a compensating tilt mirror 40, the purpose for which will be explained later on. The first collimated wavefront 38 is reflected by the tilt mirror 40 toward a beam combiner 42.

The second waveguide 34 extends along a reference path and has an end 44 at which a second reference spherical wavefront 46 is launched toward and transformed by a receiving lens 48 into a second, substantially collimated reference wavefront 50. The collimated reference wavefront 50 is transmitted to the beam combiner 42 where the first collimated wavefront 38 is superimposed on the second collimated reference wavefront so to form an interference pattern 52 which is recorded on recording means 54, such as a conventional photographic plate for a visible experiment. The interference pattern 52, produced when the first collimated wavefront 38 whose phase relationships have been affected by air turbulence is combined with the second collimated reference wavefront 50, provides information on the turbulence structure present at the entrance pupil 14 of the station 12.

It is to be expected from the cantilevered-type mounting configuration of the boom 18 that some buffeting motion is induced therein and hence in its end point 20. Obviously, if there is a lot of jitter in end point 20, the interference fringes will effectively wash out. This is because lateral motion in the end point 20 is translated into angular tilt motion in the first or object collimated wavefront 38. The combination of a steady second collimated reference wavefront 50 with a randomly gyrating first or object collimated wavefront 38 would cause fast shifts in both fringe density and pattern.

Figure 4:
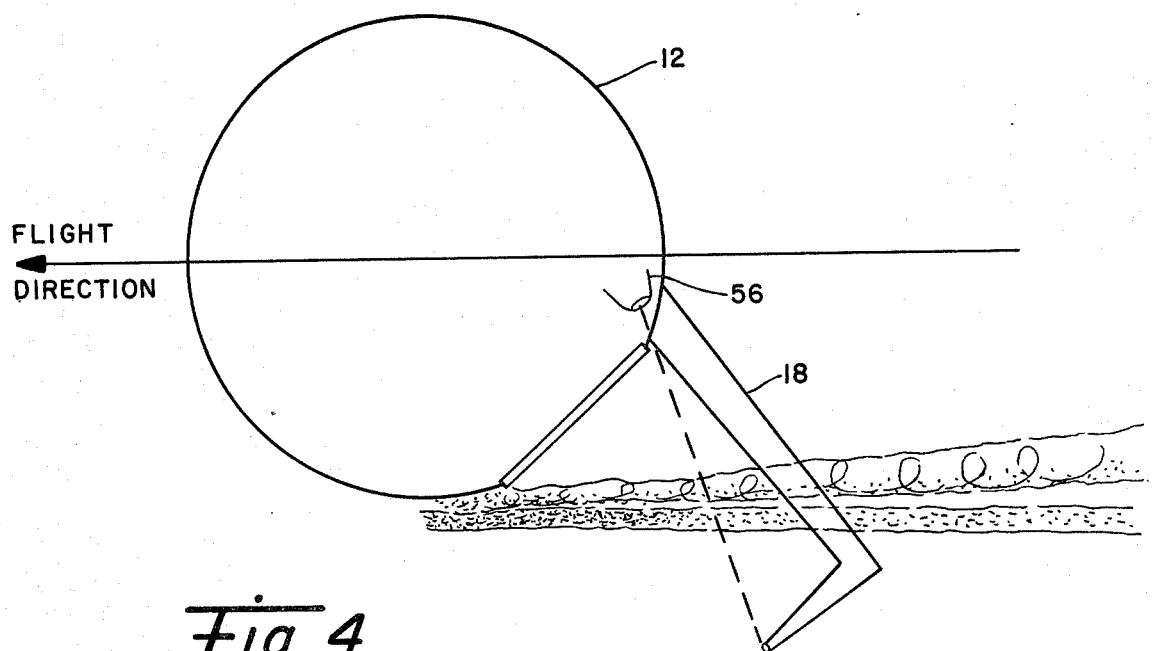
FIG. 4 is a schematic view of the apparatus of FIG. 1, showing it at one of its possible "look" angles.

Consequently, to obviate the potential problem of boom motion, the apparatus 10 preferably utilizes a conventional small visible optical tracker 56 (FIG. 4) which watches the lateral motion of the boom end point 20 and generates a signal which is sent to the compensating tilt mirror 40 to adjust the same, such as though means of a small reversible motor 58, for stabilizing the first collimated object wavefront 38 relative to the second collimated reference wavefront 50.

By using multiple waveguides, it is possible to have several interferometric experiments at different wavelengths going at the same time. In this ay there would be a good correlation of what happens in turbulence at several selected wavelengths. This would reduce the necessity for making any extrapolations and furthermore would reduce the overall time required to carry out the experiments. The rotatable turret-like station allows for addressing turbulence at any conceivable look angle. Furthermore, the boom 18 can readily be designed and positioned such that it itself does not seriously perturb the turbulence structure in front of the entrance pupil 14. The appropriate length of the boom can be determined by the extreme look angles desired for the boom, one such angle being illustrated in FIG. 4.

It is thought that the present invention and many of its attendant advantages will be understood from the foregoing description and it will be apparent that various changes may be made in the form, construction and arrangement of the parts thereof without departing from the spirit and scope of the invention or sacrificing all of its material advantages, the form hereinbefore described being merely a preferred or exemplary embodiment thereof.

Having thus described the invention, what is claimed is:

1. Turbulence measurement interferometer apparatus, comprising:
  (a) a station having an entrance pupil and optical means defining an optical axis extending through said pupil;
  (b) an aerodynamically stable boom connected to said station and having an end point spaced from said station but disposed on said optical axis;
  (c) a laser for generating a low power beam;
  (d) means for splitting said beam into first and second portions;
  (e) means for guiding said first beam portion along a first path to said boom end point from which a first spherical wavefront is launched toward said entrance pupil of said station through air turbulence between said boom end point and said station;
  (f) said optical means for receiving a portion of said first spherical wavefront and transforming the same into a first collimated wavefront;
  (g) means for guiding said second beam portion along a second reference path from which is launched a second reference spherical wavefront;
  (h) means for receiving a portion of said second spherical wavefront and transforming the same into a second collimated reference wavefront;
  (i) means for combining said first and second collimated wavefronts to form an interference pattern; and
  (j) means for recording said pattern.

2. The turbulence measurement interferometer apparatus as recited in claim 1, wherein said optical means of said station includes:
  a large concave mirror defining said optical axis and disposed remote from, and facing toward, said entrance pupil of said station;
  a small convex mirror disposed adjacent said entrance pupil and located on said optical axis between said large mirror and said entrance pupil; and a small flat mirror disposed on said optical axis at an angle thereto and located between said large concave mirror and small convex mirror.

3. The turbulence measurement interferometer apparatus as recited in claim 2, wherein:
   said large mirror is a concave elliptic mirror located centrally of said station; and
   said small mirror is a convex parabolic mirror.

4. The turbulence measurement interferometer apparatus as recited in claim 2, wherein said large concave mirror and said small convex mirror have a common focus located on said optical axis between said end point of said boom and said small mirror.

5. The turbulence measurement interferometer apparatus as recited in claim 2, wherein said angularly disposed small flat mirror produces an afocal output in the form of said collimated wavefront.

6. The turbulence measurement interferometer apparatus as recited in claim 1, wherein said means for guiding said first and second beam portions each comprises a self-focusing optical waveguide in the form of a solid fiber optic.

7. The turbulence measurement interferometer apparatus as recited in claim 6, wherein said self-focusing optical waveguide for guiding said first beam portion is disposed along said boom from said station to said end point of said boom.

8. The turbulence measurement interferometer apparatus as recited in claim 1, wherein said means for guiding said first and second beam portions are of substantially equal length.

9. The turbulence measurement interferometer apparatus as recited in claim 1, further comprising:
   (k) a compensating tilt mirror disposed for receiving said first collimated wave prior to its being combined with said second collimated reference wavefront; and
   (l) means for tracking lateral motion of said end point on said boom and for generating a signal which is sent to said compensating tilt mirror to adjust the same for stabilizing said first collimated wavefront relative to said second collimated reference wavefront.

* * * * *